(12) United States Patent
Haessler (10) Patent No.: US 7,210,933 B2
(45) Date of Patent: May 1, 2007

(54) IMPLANT SYSTEM

(75) Inventor: Dieter Haessler, Oppenheim (DE)

(73) Assignee: Friadent GmbH, Mannheim (DE)

( * ) Notice: Subject to any disclaimer, the term of this patent is extended or adjusted under 35 U.S.C. 154(b) by 176 days.

(21) Appl. No.: 10/468,623

(22) PCT Filed: Feb. 1, 2002

(86) PCT No.: PCT/EP02/01057

§ 371 (c)(1),
(2), (4) Date: Mar. 8, 2004

(87) PCT Pub. No.: WO02/062255

PCT Pub. Date: Aug. 15, 2002

(65) Prior Publication Data

US 2004/0146834 A1    Jul. 29, 2004

(30) Foreign Application Priority Data

Feb. 2, 2001   (DE)   ................ 101 05 227

(51) Int. Cl.
*A61C 8/00* (2006.01)
(52) U.S. Cl. .................................... 433/174
(58) Field of Classification Search ......... 433/173–176
See application file for complete search history.

(56) References Cited

U.S. PATENT DOCUMENTS 4,787,848 A * 11/1988 Ross .................. 433/165
5,000,686 A    3/1991 Lazzara
5,078,607 A * 1/1992 Niznick .................. 433/174
5,199,873 A    4/1993 Schulte et al.
5,246,370 A * 9/1993 Coatoam ............... 433/173

(Continued)

FOREIGN PATENT DOCUMENTS

DE   3800368   7/1988

(Continued)

OTHER PUBLICATIONS

1986 Zahnaertzliche Implantologie (Case Key, Dental Implantology) Gerd K.H. Fallschuessel et al. Quintessenz Verlags-GmbH pp. 254-255.

(Continued)

*Primary Examiner*—Cary E. O'Connor
(74) *Attorney, Agent, or Firm*—Jordan and Hamburg LLP (57) ABSTRACT

The invention relates to an implant system containing at least one drill and one implant, particularly a dental implant, which can be screwed into a bore hole made in a bone by means of a drill. Preferably, the implant comprises a self-cutting screw with a thread core. The aim of the invention is to further develop an implant system which guarantees high primary stability for a wide variety of bone qualities and requires little technical complexity. According to the invention, the implant and the drill are co-ordinated in such a manner according to bone quality that a compressed zone arises when the implant is screwed into the implant in the bone. The size of the compressed zone is greater for low bone quality than for high bone quality.

16 Claims, 6 Drawing Sheets

U.S. PATENT DOCUMENTS

| | | | | |
|---|---|---|---|---|
| 5,741,267 | A | * | 4/1998 | Jorneus et al. ............... 606/102 |
| 5,795,160 | A | * | 8/1998 | Hahn et al. .................. 433/174 |
| 5,816,812 | A | * | 10/1998 | Kownacki et al. .......... 433/174 |
| 5,954,504 | A | | 9/1999 | Misch et al. |
| 5,967,783 | A | * | 10/1999 | Ura ............................ 433/174 |
| 6,203,324 | B1 | * | 3/2001 | Wils .......................... 433/173 |
| 6,364,663 | B1 | * | 4/2002 | Dinkelacker ................ 433/173 |
| 6,402,515 | B1 | * | 6/2002 | Palti et al. .................. 433/174 |

FOREIGN PATENT DOCUMENTS

| | | |
|---|---|---|
| DE | 4332075 | 3/1994 |
| DE | 4415076 | 11/1995 |

OTHER PUBLICATIONS

XIVE Surgery brochure.

* cited by examiner

IMPLANT SYSTEM

BACKGROUND OF THE INVENTION

The invention relates to an implant system.

An implant of this type is known, for example, from the U.S. Pat. No. 5,000,686. It is a dental implant with a self-cutting external thread. For inserting the implant, a borehole, the diameter of which corresponds essentially to the core diameter of the implant, is introduced into the jawbone-a drill. Subsequently, the implant is screwed into said borehole in the bone. In the case of the previously known implant, the core diameter of the thread, starting out from a cervical region, tapers towards an apical region, the depth of the thread being less in the cervical region than in the apical region. By these means, it is taken into account that the density of the bone is greater in the region of its upper edge than in lower lying areas. Classifications have therefore been proposed for different bone densities (qualities), for example, a classification of the alveolar bone into classes DI to DIV. The bone quality DI stands for a very cortical hard bone, while the bone quality DIV stands for a very spongy bone with very thin surrounding cortical substance. Such classifications of the bone quality take into consideration the strength, the size of pores, the compactness, the homogeneity, the density and the like of the bone.

SUMMARY OF THE INVENTION

Starting out from this, it is an object of the invention to propose an implant system, particularly with a dental implant, which enables the maximum, primary stability of the implant to be achieved in spite of the different starting conditions in the bony stratum. The implant system is to make it possible to insert the implant in a simple manner and to ensure the highest primary stability in all bone qualities. A system and an implant are proposed, in order to be able to screw the implant functionally reliably into different bone qualities and to attain the highest possible primary stability.

The inventive implant system enables the bony stratum to be prepared without problems by the drill or drills and the appropriately coordinated implant to be prepared as a function of the bone quality. The implant and drill or drills for preparing the bone stratum and for introducing the borehole are matched to one another so that an "internal condensation effect" is achieved as the implant is screwed in, particularly in the cervical bone region. The axial and/or radial dimensions of the zone in the bone, which is to be consolidated during the screwing in of the implant, are larger for bones of lower quality. For bones of different quality, the drill geometry and/or the depth of insertion of the drill are adapted; however, the design of the implant is not changed. A special (crestal) drill is provided for hard bones in the marginal or cervical region. Advisably, the zone, which is to be consolidated, lies in the crestal or cervical bone region, in the region of the opening in the upper edge of the bone and, moreover, preferably at a specified distance from the latter. Pursuant to the invention, especially the diameters of the thread core and the drill, assigned to the cervical bone region, are matched to one another so that, the softer the bone, the greater is the compression specified for the bone.

For the bone with the greatest possible hardness, especially of bone quality DI, the matching preferably is such that there is no condensation. When the implant is screwed in, the bone is consolidated particularly in the sub-cervical region, a high primary stability and a high-grade anchoring of the implant being ensured even in the case of bones of quality DII, DIII or DIV. On the other hand, pursuant to the invention, the implant is not pressed too strongly cervically into the bone, so that absorption of the bone, which would result from this, is avoided. Since the internal compression takes place sub-cortically in the spongy region while the implant is being screwed in, undesirable, disadvantageous excessive bone stresses, as caused, for example, by consolidating and by tapping with the appropriate, suitable hand instruments, is avoided. Comfort for the patient is improved decisively by this technique. The size of the zone, which is to be consolidated, is determined especially by specifying the axial depth of a bone region, which starts out from the upper edge of the bone. In addition or alternatively, the core diameter of the crestal or cervical thread region and the borehole diameter of the cervical bone region can be specified as a function of the bone quality by the cervical or secondary drill for specifying the size and/or the cross section of the zone in the bone, which is to be consolidated while the implant is being screwed in.

Advantageously, a pilot drill is provided for introducing an initial pilot borehole in the bone, especially the jawbone, the depth of the pilot borehole being specified essentially by the length of the implant. In addition, the position and direction of the implant is fixed. Especially after the pilot borehole or preliminary borehole is introduced, a primary borehole is introduced pursuant to the invention by a primary drill, the diameter of the preliminary borehole being less than that of the primary borehole. The diameter of the primary drill and, accordingly, of the primary borehole corresponds at least approximately to the core diameter in the apical region of the implant. The apical end region of the primary borehole is also referred to below as the first borehole region. Within the scope of the invention and, for example, in the case of a conically tapering thread core in the cervical region of the implant, the primary borehole and/or the drill, intended for this borehole, can also be constructed correspondingly tapered at least for this region. Preferably, the bone quality is determined while drilling the pilot borehole and/or by drilled-out bone material. Furthermore, the bone quality can be determined by suitable diagnostic measures already before the preliminary borehole or primary borehole is introduced, for example, by x-rays or nuclear spin tomography. Subsequently, a secondary borehole, the depth of which advantageously corresponds to the bone quality, is introduced by the drill, which is constructed pursuant to the invention and referred to in the following also as cervical or secondary drill. In the case of a dense, compact bone, for example, of bone quality DI, a comparatively large depth is specified, which corresponds at least approximately to the length of the cervical region of the implant. The depth of the secondary borehole for a very hard bone is specified to be approximately half the total length of the implant and/or at least approximately equal to the depth of the apical region. Preferably, the secondary drill has means for specifying the depth of drilling. These means are formed especially as markings at the outer surface or as stops or stop elements, which, if necessary, are mounted on the secondary drill. These means are constructed especially so that the drilling is stopped as soon as these means reach the upper edge of the bone.

The diameter of the secondary drill and/or of the secondary borehole advantageously is specified so that the implant can be lowered and/or screwed in without problems even into the dense, compact bone with out overloading the bone. For bones of low bone quality, the secondary borehole has a lesser depth. In the limiting case involving a soft bone, especially a bone corresponding to quality DIV, the depth of the secondary borehole is only such, that essentially only the cortical substance at the edge is removed. The condensation zone therefore commences at a distance from the upper edge of the bone, which is specified pursuant to the invention. Pursuant to the invention, the depth of the secondary borehole varies with the hardness of the bone, that is, the "harder" the bone, the deeper the borehole. Subsequently, the implant is screwed in to the borehole, which has been prepared pursuant to the invention, the apical region of the thread of the implant engaging the apical region of the primary borehole in a self-cutting manner. Since the diameter of the secondary borehole is at least approximately equal to the core diameter of the cervical region of the implant, the implant can be screwed without problems into a hard bone. In the case of soft bones, the screwing of the thread core, which is widened in comparison to the borehole or the drill in the cervical region of the implant, into the zone of the cervical bone region, which has not been drilled out, brings about an internal condensation effect, so that the bone in said zone of the cervical region is consolidated and, pursuant to the invention, the primary stability for high-grade anchoring of the implant is achieved also in soft bones.

Advantageously, only two drills are therefore required for the set of instruments for introducing the primary borehole and the secondary borehole in accordance with the bone quality. The drill for the second borehole advantageously has means, especially markings, which correspond to the depth, which is to be introduced. It should be noted here that implants with different diameters and/or different lengths usually are available. Consequently, the set of instruments contains drills matching the diameters of the implants and, moreover, in each case a drill for the primary borehole and a drill for the secondary borehole of the respective implant size and, optionally, also a preliminary drill. For implants of the same diameter but of different length, the same set of instruments are used, the primary dill and the appropriately provided preliminary drill having suitable means, such as markings or stop elements, for specifying the depth of the borehole, which corresponds to the length of the implant. Pursuant to the invention, the apical region of the thread, especially of the primary dill for implants of the same diameter and different length, is formed identically, the apical regions of the thread of the implants also being formed identically.

In accordance with the comments above, the implant contains a continuous thread, the core diameter of which is larger in the cervical region than in the apical region. The depth of the thread in the cervical region is, in particular, of the order of $1/10$ to $4/10$ mm and, in the apical region, advantageously between $4/10$ to $7/10$ mm. The thread core diameter in the apical region of the implant preferably is smaller by a specified amount than the thread core diameter in the cervical region and, in particular, corresponds essentially to the diameter of the primary drill in the second or apical region of the drill. The lengths of said thread regions are specified to be at least approximately identical and, moreover, preferably for all implants of the same diameter but of different lengths. For longer implants, an intermediate region is provided pursuant to the invention, the thread of which is essentially identical with that of the apical region and/or the thread core of which has a diameter, which is smaller than that in the cervical region by a specified amount.

Furthermore, within the scope of the invention, the implant can also be formed as a stepped screw, which has at least two thread regions or steps with different external diameters, the step at the apical end of the implant having the smallest external diameter. Such step implants are known, for example, from the EP patent 0 438 048. It is also of decisive importance for such embodiments that, especially by matching the diameter or diameters in the cervical region of the implant and the diameter or diameters of the boreholes in the cervical bone region and/or the depths of such regions as a function of the bone quality, an internal condensation or consolidation of the bone in a zone of specifiable magnitude is achieved preferably in the sub-cervical region, when the implant is screwed in.

Moreover, within the scope of the invention, other drill sets can also be provided as an alternative to the drill for the initial primary borehole and the drill for the secondary borehole. For example, several, especially four drills with thread steps of different lengths in the cervical region can be provided for implants of the same diameter for the secondary borehole, the lengths of the steps being matched to the quality of the bones and the diameters, adjoining the apical end, being matched to the diameter of the apical region of the thread of the implant. Moreover, the external diameters of the, for example, four drills in the cervical region can be specified differently depending on the different bone qualities. In this connection, the primary drilling can optionally also be carried out with a drill, the diameter of which is smaller than the core diameter of the apical region of the thread of the implant. Moreover, the use of a primary drill can optionally be omitted and the borehole can be introduced into the bone in a single step with a single drill of the set of four drills in accordance with the four bone qualities.

Further embodiments and special configurations of the invention are given in the following detailed description of certain preferred embodiments.

BRIEF DESCRIPTION OF THE DRAWINGS

The invention is described in greater detail in the following by special examples, the invention however, not being limited to these examples. In the drawings.

DETAILED DESCRIPTION OF CERTAIN PREFERRED EMBODIMENTS

Figure 1:
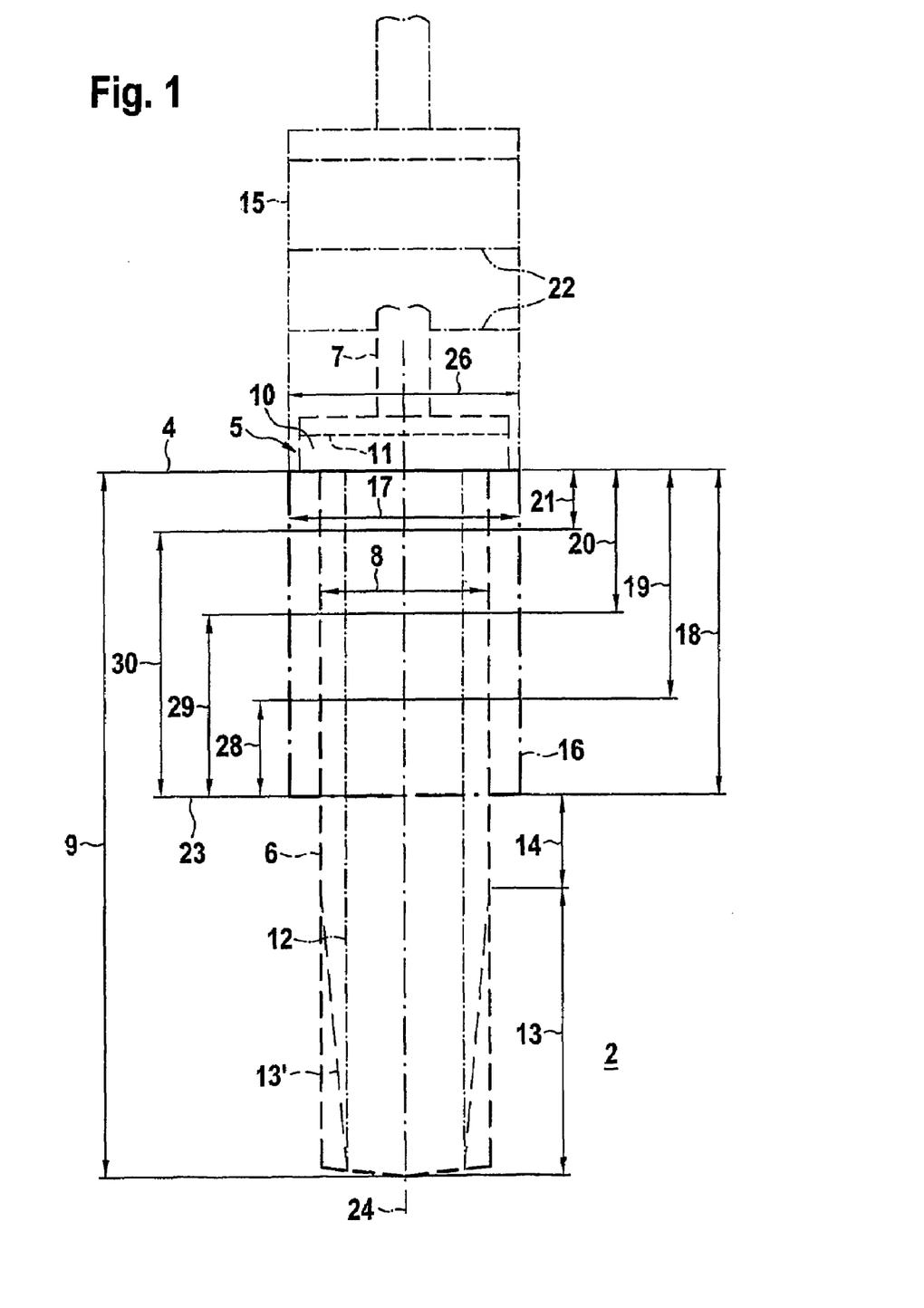
FIG. 1 is a diagrammatic representation of the drill and of the boreholes introduced into the bone.

FIG. 1 diagrammatically shows a section through a bone 2 with an upper edge 4, in which a primary borehole 6 or a first drilling region, indicated by broken lines, is introduced by a primary drill 5. The primary drill 5, which is also shown by broken lines, contains a shaft, which can be inserted in a known manner in a drilling device. The primary borehole 6 or the first drilling region has a diameter 8 and a length 9, which is at least equal to the length of the implant, which is not shown here. Outside of the bone 2 or above the upper edge 4, the drill 5 has a stop or a radial expansion 10 and at least one marking 11, which form means for specifying the depth, of primary borehole 6. Furthermore, especially below the expansion 10, stop means can be provided for specifying or limiting the depth of introduction. Accordingly, boreholes, which are longer or deeper than the length 9 shown, can also be introduced with the same primary drill 5.

The primary drill 5 or the primary borehole 6 contains an apical region 13, which is constructed to correspond to the apical region of the implant. The apical end region 13 is constructed identically for all implant lengths, whereas the axial length of an intermediate region 14 of the primary borehole 6 is specified in accordance to the length of the implant. For implants of the same diameter but different length 9, which preferably is specified in the region to be between 8 and 20 mm, the same primary drill 5 is used accordingly, the depth of introduction in the bone 2, however, being specified. The intermediate region 14, which, in particular, is cylindrical, advisably has the same diameter 8 as the cervical region, which adjoins in the direction of the upper edge 4 of the bone. Particularly in the apical end region 13, the drill 5 may also have a slightly conical external contour to correspond to that of the implant. This is indicated by the broken line 13'. Previously, a preliminary borehole can be introduced in the bone 2 by a preliminary drill as indicated by the line 12 of dots and dashes. The diameter 8 of the primary drill 5 or the primary borehole 6 corresponds essentially that of the thread core in the apical region of the implant, which is not shown here.

After the introduction of the primary borehole 6, a secondary borehole 16, with the crestal cervical diameter 17, was introduced by a secondary drill 15. Pursuant to the invention, the depth of the secondary borehole 16 and/or of a corresponding borehole region of the total borehole is specified to correspond to the different bone qualities, for example, DI to DIV. For the bone quality DI, that is, for a dense compact bone, the greatest depth is 18, for the bone quality DII the depth is 19, for the bone quality DIII the depth is 20 and for the bone quality DIV, that is for a very spongy bone with a very thin surrounding cortical substance, the depth is 21. The drill or secondary drill 15, shown by lines and dots and dashes, preferably has means for the depth of introduction, these means preferably being formed by markings 22, which are disposed at the outer surface of the drill 15. These marking 22 are spaced apart from one another to correspond to the depths of introduction 18 to 21.

The lower edge of a cervical thread region of an implant inserted in the direction of the longitudinal axis 24 into the borehole of the bone is indicated by the means of a line 23. The cervical region of the thread has a core diameter 26 which is, at least approximately equal in size to that of the exterior diameter of the secondary drill 15 or to the internal diameter 17 of the secondary borehole 16.

After the implant is inserted, the lower edge of the implant, corresponding to the line 23 of the cervical thread region, is separated from the upper edge 4 of the bone by a distance, which is essentially equal in size to the depth 18 for the best bone quality DI. Accordingly, for this bone quality, the implant can be screwed in a known manner and/or with the usually permissible expenditure of force into the bone 2, the thread flanks of the cervical thread region cutting into the surrounding cervical bone region over the region of the secondary borehole extending to the depth 18. In the event of a lesser bone quality DII, the secondary borehole is introduced only to the depth 19, so that the primary borehole 6 with the diameter 8 adjoins apically thereon. Accordingly, a zone 29 is present in the cervical bone region between the lower edge of the secondary borehole of depth 19 and the line 23. As the implant is being screwed in, the bone material in this zone 29 is displaced laterally and consolidated by the cervical thread core. Analogously, zones of the bone, which are to be consolidated as the implant is screwed in, are created corresponding to the depths 20, 21 for bones of qualities DIII and DIV. For a relatively soft bone or for the lowest bone quality DIV, the secondary borehole is expanded corresponding to the depth 21 by the secondary drill 15 to the diameter 17 only in the region adjoining the upper edge 4 of the bone. In the region with the depth 21, adjoining the upper edge 4 of the bone, there is therefore no condensation and any undesirable tearing out of the bone is thus avoided reliably. In this region, a preferably thread-free neck region is in contact with the bone.

Figure 2:
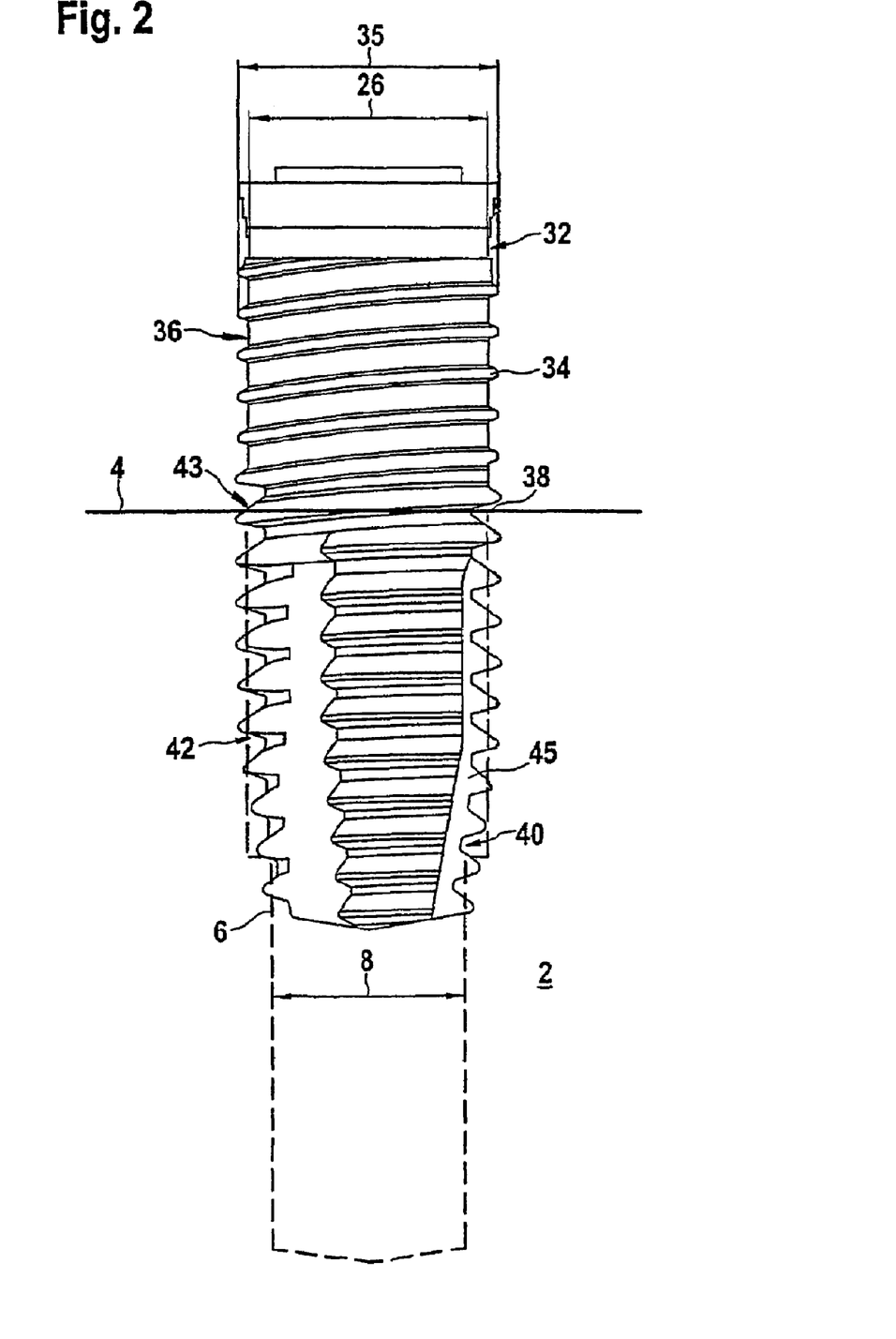
FIG. 2 illustrates a partially inserted implant.

FIG. 2 shows the borehole so prepared and having an opening 38 at the upper edge 4, with a partially inserted implant 32, which is constructed as a screw implant with a self-cutting, continuous outer thread 34 with an external diameter 35 of the tip of the thread. In the cervical region 36, which, according to the drawing, is above the upper edge 4, the thread 34 of the implant 32 has a core diameter 26, which is larger, by a specified amount, than the core diameter 40 in the apical region 42. The core diameter 40 is at least approximately as large as the diameter 8 of the primary borehole 6. The lower edge of the cervical region 36 lies here level with the upper edge 4 of the bone. As can be seen, the implant in the apical region 42 is formed so as to taper conically towards the apical end. Adjoining the cervical region 36 in the direction of the apical end, a transition region 43 is provided, in which the core diameter 26 changes over at least approximately continuously into the core diameter 40. This transition region 43 extends preferably over at least 360° or over one thread and especially over approximately 720° or two threads. In particular, at most three threads are present. The length of the transition region 43 is significantly less than that of the cervical region 36 and/or of the apical region 42. Accordingly, as the implant is screwed into the borehole prepared in accordance with the above comments, the bone is displaced gently and radially into the tissue and consolidated by the transition region 43. As can be seen, the implant has cutting grooves 45 in the apical region 42, advisedly such cutting grooves being distributed over the periphery. Pursuant to the invention, the core diameter 26 of the implant thread in the cervical region 36 is larger by a specified amount than the diameter 8 of the primary borehole or of the drill, with which the latter was introduced into the cervical bone region. Accordingly, as the implant 32 is screwed further into the bone, condensation of the bone in the zones explained above by FIG. 1 takes place in the sub-cervical region of the bone because of this diameter difference.

Alternatively, within the scope of the invention, the cervical bone region can be prepared by the drill so that, instead of the different depths in the cervical region, different diameters of the primary borehole are introduced into the bone by appropriately constructed drills. A lesser diameter is specified for a soft bone, for example, of quality DIV, than for a harder bone, for example, of quality DII. Preferably, a diameter difference between the thread core and the borehole diameter of at least 0.05 mm is specified in the case of a quite hard cortical bone, for example, of the bone quality DI.

Figure 3:
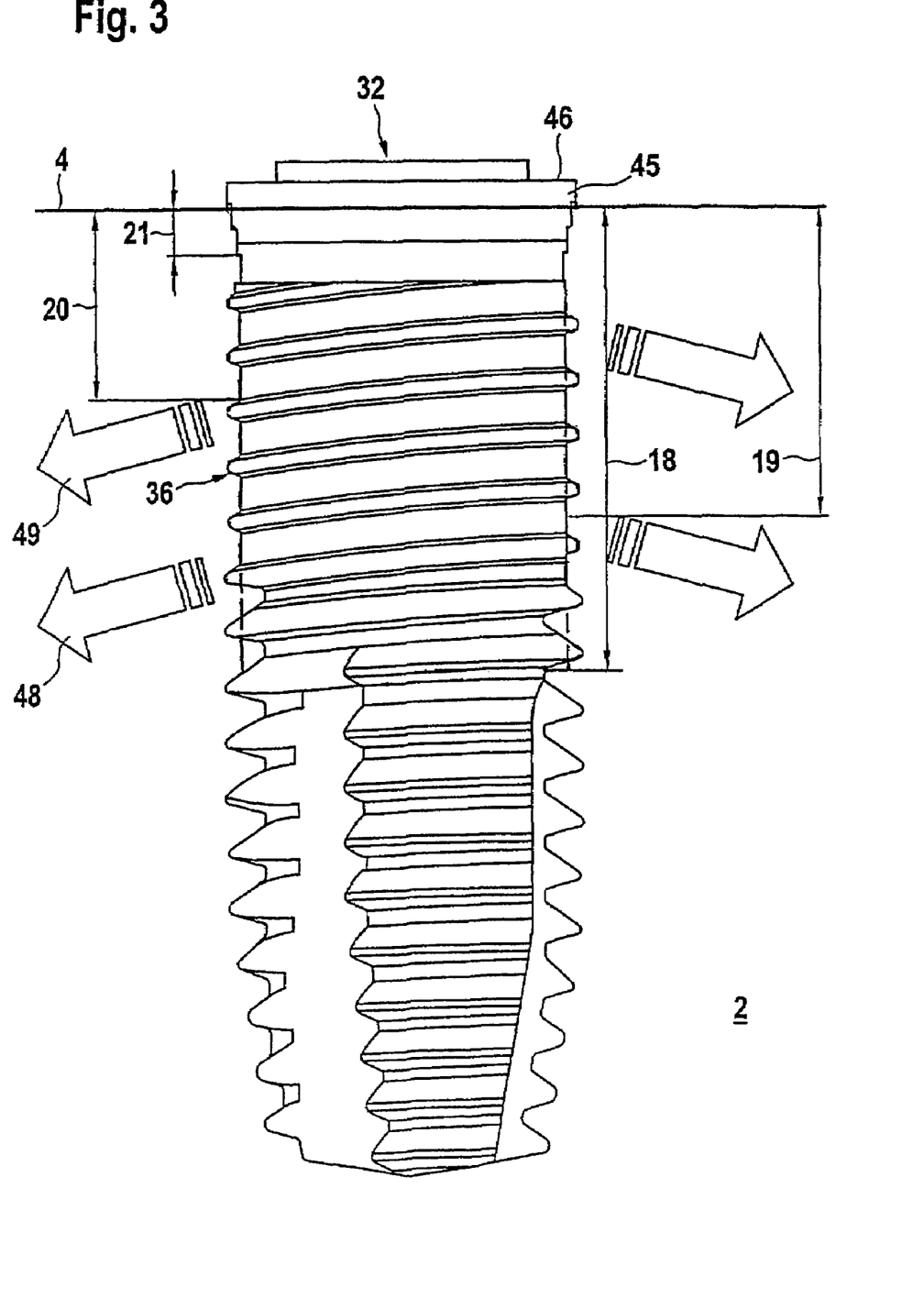
FIG. 3 illustrates a completely inserted implant.

FIG. 3 shows the implant 32, which is inserted completely in the bone 2 and the preferably thread-free neck region 45 of which passes through the upper edge 4 of the bone. The neck region 45 is in contact with the cortical material, as a result of which a stable anchoring of the implant in the cortical material is achieved in an advantageous manner. For the bone quality DI, in accordance with the depth 18 of the secondary borehole, a ring-shaped bone core is removed completely so that the implant can be lowered and screwed essentially freely and without problems into the bone, the thread being screwed into the bone in a known manner. For softer bone qualities, corresponding to depths 19, 20 and 21, the bone assigned to the cervical region 36 of the implant 32 is displaced laterally and condensed in the zones described above, as indicated by arrows 48, 49.

Figure 4:
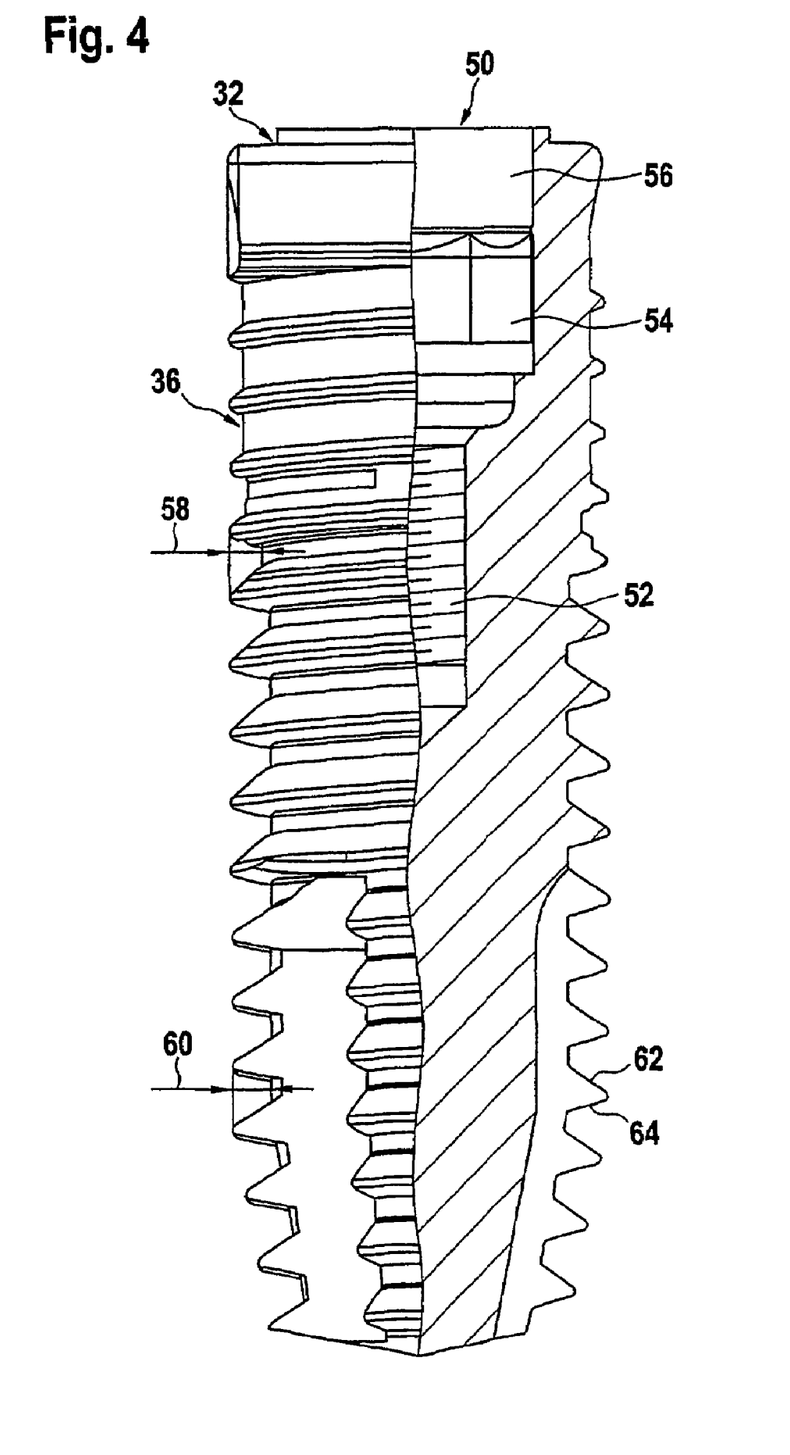
FIG. 4 illustrates the implant partly in a lateral view and partly in an axial section and FIGS. 5 to 12 illustrate sections through bone with four different bone qualities and the inserted implants.

FIG. 4 shows the implant 32 partially in a side view and partially in a sectional view. The implant preferably is a dental implant and/or constructed as a titanium screw implant and contains an inner borehole 50 with an internal thread 52 for the holding screw, with which a setting upper part can be connected with the implant 32 in a known manner. The borehole 50 furthermore contains seating means 54, especially in the form of a hexagon socket, for a tool, with which the implant 32 can be screwed into the bone. Furthermore, the borehole 50, adjoining the plateau 46, contains a centering surface 56, especially a cylindrical centering surface 56, for the setting-up element. As can be seen, the radial depth 58 of the thread in the cervical region 36 increases towards the apical region 42. In the apical region 42, the implant has a radial thread depth 60.

In a particular development, the lead at the upper side 62 of the thread flanks is less by a specified factor than the lead at the underside 64. Accordingly, the lead at the upper side 62, particularly of the order of ⅒, is less than that at the underside 64. Accordingly, with increasing height, the profile at the thread flank becomes narrower with the result that, as the implant is screwed in, the increase in friction in the bone becomes less. By these means, it is avoided that the friction between the implant and the bone in "a hard bone" increases with increasing implant length. Accordingly, the lead at the upper side 62 is specified, especially, to be of the order of 0.86 and, at the underside 64, to be of the order of 0.87.

Example of an Instrument Set and of an Implant

| | |
|---|---|
| Diameter of the preliminary drill | 2.0 mm |
| Diameter of the primary drill | 3.5 mm |
| Diameter of the secondary drill | 3.9 mm |
| Cervical core diameter 26 of the implant | 3.8 mm |
| Apical core diameter 40 of the implant | 3.4 mm |
| Crestal thread depth 58 | 0.2 mm |
| Apical thread depths 60 | 0.5 mm |

Figure 5:
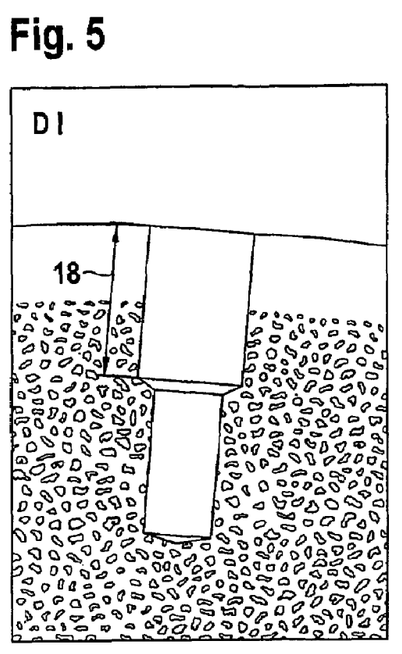
Figure 6:
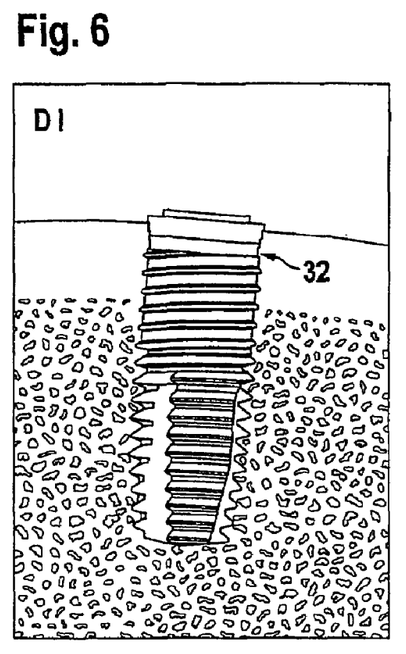

FIG. 5 diagrammatically shows a section through a dense, compact bone corresponding to bone quality DI. The borehole, introduced into this bone, has the comparatively large depth 18 in the region adjoining the upper edge 4. According to FIG. 6, the implant 32 is screwed into the borehole, so produced. As can be seen, the cervical region of the implant 32 essentially is as long as the depth 18, so that the implant 32 can be screwed without problems and/or freely into the dense and compacted bone.

Figure 7:
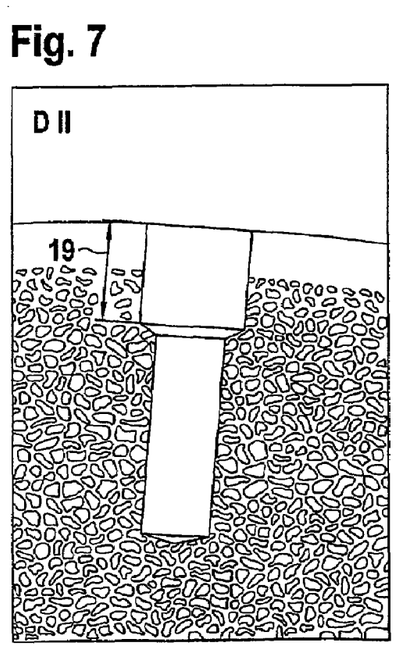

FIG. 7 diagrammatically shows a porous, compact bone of quality DII. In comparison to FIG. 5, the depth 19 for the secondary borehole is less. According to FIG. 8, the implant 32 is screwed once again into the borehole so prepared. Since the length of the cervical region of the implant 32 is greater that the depth 19 of the assigned borehole part, the bone in zone 28 in the cervical region is consolidated correspondingly, so that, in spite of a reduced bone quality, a high primary stability is assured.

Figure 8:
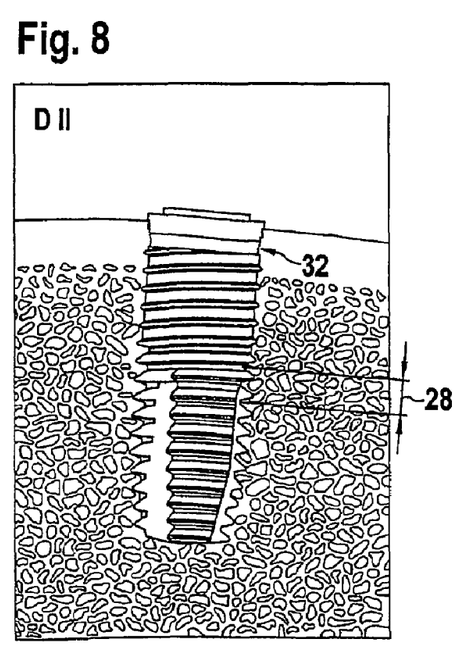
Figure 9:
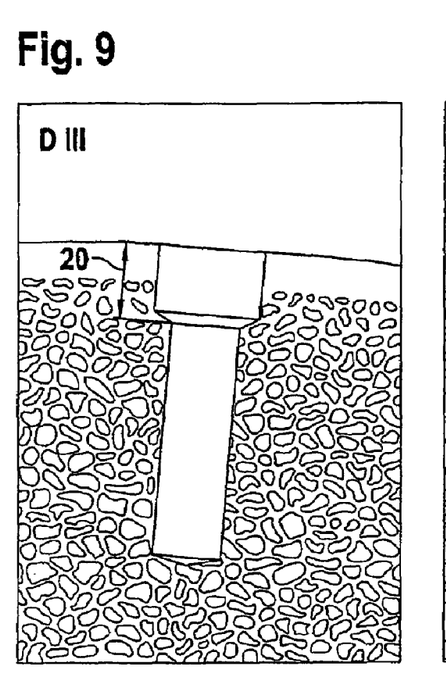
Figure 10:
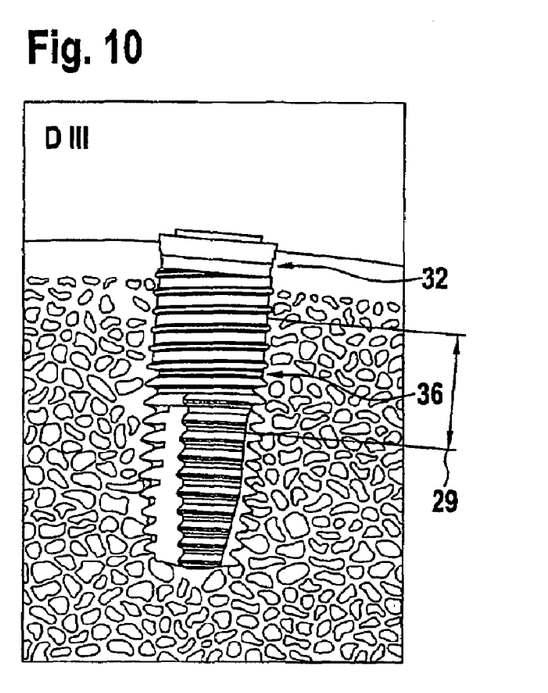

FIG. 9 shows a section through a relative porous spongy bone with comparatively thin, surrounding cortical material corresponding to bone quality DIII. The depth 20 of the secondary borehole in this bone is even less. Consequently, as shown in FIG. 10, the zone 29 of the bone, which is enlarged in comparison to FIG. 8, is consolidated by the cervical region 36 of the implant 32.

Figure 11:
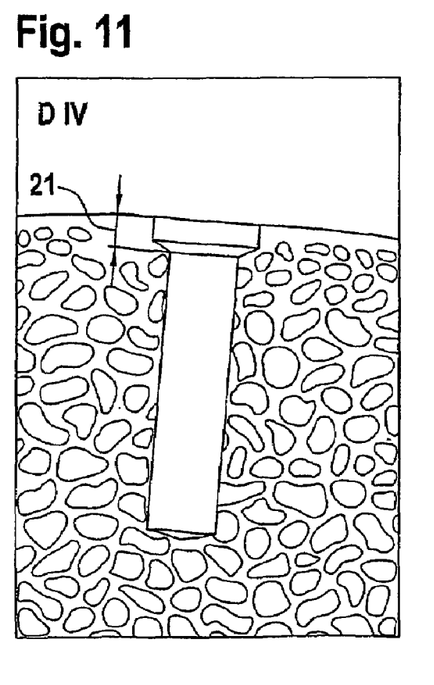
Figure 12:
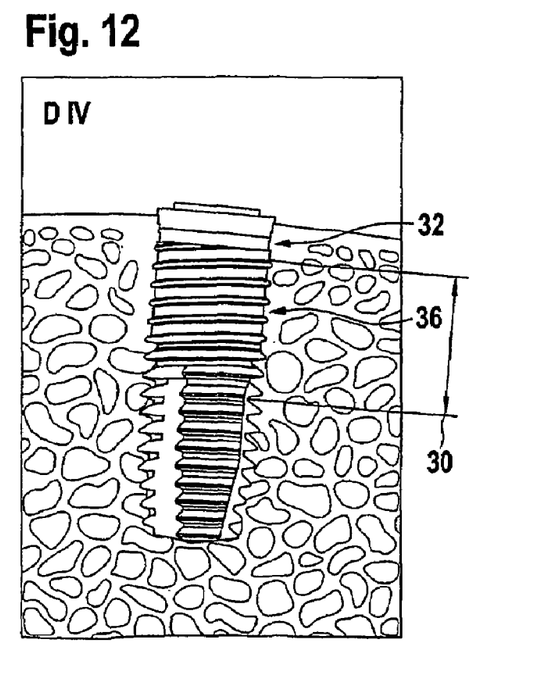

Finally, FIG. 11 shows a very spongy bone of quality DIV, which is surrounded by very thin cortical material. An extremely slight depth 21 is specified for the secondary borehole. Accordingly, as shown in FIG. 12, the bone in zone 30 is consolidated practically over the whole length of the cervical region 36 of the implant 32, so that the required primary stability for a high grade anchoring of the implant is assured.

It should be noted explicitly here that, in the implant system, the same implants 32 with the same diameter are always used, independently of the bone quality, the high primary stability being assured by a depth of the secondary borehole, specified for the bone quality, and/or by the size of the zones assigned especially to cervical implant region, which are matched to the particular bone quality. Moreover, the same drill is always used for implants 32 of the same diameter but of a different length. It is self-evident that the implant system for implants of other diameters furthermore has drills with appropriately matched diameters. For example a complete implant system for implants with different diameters of, for example, 3 mm, 3.4 mm, 3.8 mm, 4.5 mm, 5.5 mm comprises in each case, an assigned set of drills, particularly preliminary drills, primary drills and secondary drills, with which the boreholes are produced in the bones for implants of the respective diameters but of different lengths in accordance with the comments above.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

The invention claimed is:

1. A method of implanting an implant in a bone, said method comprising:
    identifying bone quality of said bone as being selected from a predefined plurality of bone quality categories including at least a first and a second bone quality category;
    the first bone quality category being more dense than the second bone quality category;
    providing at least one drill for producing at least one borehole in bone; and
    providing an implant, screwable into said bone through said borehole,
   wherein said drill and said implant being matched according to bone quality, such that when said implant is screwed into said bone, a consolidated zone is produced;
    said consolidated zone having an axial length directly related to said bone quality; and
    whereby the size of said consolidated zone is smaller for bone quality in the first category than the size of said consolidated zone for bone quality in the second category.

2. The method of claim 1, wherein said implant has a self-cutting screw with a threaded core.

3. The method of claim 2, wherein said implant has an apical region, a cervical region, and a transition region therebetween; and
    further comprising at least one selected from the group consisting of (1), (2), where:

(1) a core diameter of said implant in said transition region decreases continuously in a direction toward said apical region; and (2) said transition region extends a distance corresponding to a peripheral angle of from 360° to 1,080°, as measured traversing a circularly helical path along said threaded core.

4. The method of claim 3, wherein:

there are two drills, coaxial to one another, so that a first drill is a primary drill for producing a primary borehole in said cervical region, and has a first diameter; and a second drill is a secondary drill and has a second diameter; and further comprising at least one selected from the group consisting of (1), (2), (3), where:

(1) said second diameter is greater than said first diameter;

(2) a core diameter of said implant in said cervical region is the same as said second diameter; and (3) an external diameter, as measured from crest to crest of a tooth of a thread of said implant in said cervical region of said implant is greater than said second diameter.

5. The method of claim 4, wherein said secondary drill has indicia relating a depth to which said implant is to set in said bone, to said identified bone quality category.

6. The method of claim 4, further comprising at least one selected from the group consisting of (1), (2), (3), (4), where:

(1) said consolidated zone is in said cervical region of said implant;

(2) said consolidated zone is defined by a second borehole, commencing at a spongiosa region of said bone;

(3) said consolidated zone is at a distance from an upper edge of said bone; and (4) said second borehole is made in said bone as a function of bone quality category, such that said implant is freely screwable into said bone if said bone quality category is said first bone quality category.

7. The method of claim 6, further comprising at least one selected from the group consisting of (1), (2), (3), where:

(1) said boreholes are made such that said second borehole is in a region corresponding to said cervical region of said implant, and has a depth that is a direct function of said identified bone quality category, with said depth being greater for bone of said first bone quality category than bone of said second bone quality category;

(2) a length of said primary borehole is at least as large as a length of said implant; and (3) a diameter of said primary borehole is as large as a core diameter of said implant in said apical region.

8. The method of claim 7, further comprising at least one selected from the group consisting of (1), (2), (3), (4), where:

(1) said second borehole is produced by a secondary drilling;

(2) said second borehole is in said cervical region of said implant;

(3) said second borehole commences at an upper edge of said bone; and (4) said second borehole has a diameter as large as a core diameter of said implant in said cervical region.

9. The method of claim 8, wherein said plurality of bone quality categories includes four Lekhom and Larb categories wherein a first of said Lekhom and Larb categories includes bone qualities of a higher density than a fourth of said Lekhom and Larb categories:

further comprising at least one selected from the group consisting of (1), (2), (3), where:

(1) said depth of said secondary borehole is greater in a bone of said first bone quality category than a bone of said second bone quality category;

(2) said depth of said second borehole is half as large for bone of said first bone quality category of said Lekhom and Larb categories as a total length of said borehole; and (3) said depth of said second borehole is the same size as a thickness of cortical material surrounding said bone for bone of said fourth bone quality category of said Lekhom and Larb categories.

10. The method of claim 1, wherein said consolidated zone is in a sub-cervical region of said implant.

11. The method of claim 1, wherein said consolidated zone has a specified depth commencing at a predetermined distance from an upper edge of said bone and continuing to said upper edge of said bone.

12. The method of claim 1, wherein said threaded core of said implant has a diameter in at least one of said consolidated zone and a cervical region of said implant, said diameter being greater than a diameter of said drill.

13. The method of claim 1, wherein dimensions of said consolidated zone are a function of bone quality so that at least one of a length of said consolidated zone, and a difference in diameter of said consolidated zone from one end of said consolidated zone to an opposite end of said consolidated zone is greater for a bone quality in said second category than for a bone quality of said first category.

14. The method of claim 1, wherein:

there are two drills, including a primary drill for producing a primary borehole and a secondary drill for producing a secondary borehole; and so that said primary borehole has a depth equal to a length of said implant, and said secondary borehole is made to a specified depth from an upper edge of said bone, that is a function of said bone quality category.

15. The method of claim 14, wherein:

said secondary drill has indicia relating a depth to which said implant is to be set in said bone, to said bone quality category;

drilling of said secondary borehole is terminated when an upper edge of said bone corresponds to one of said indicia corresponding to quality category of said bone;

thereby matching depth of said secondary borehole to said quality category of said bone.

16. Implant system being implanted according to the method of claim 1.

* * * * *